(12) United States Patent
Knapp

(10) Patent No.: US 7,135,189 B2
(45) Date of Patent: Nov. 14, 2006

(54) COMPOSITIONS AND TECHNIQUES FOR LOCALIZED THERAPY

(75) Inventor: David Knapp, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 779 days.

(21) Appl. No.: 09/935,442

(22) Filed: Aug. 23, 2001

(65) Prior Publication Data

US 2003/0045865 A1   Mar. 6, 2003

(51) Int. Cl.
A61F 13/00 (2006.01)
A61F 2/00 (2006.01)

(52) U.S. Cl. ..................... 424/422; 424/423

(58) Field of Classification Search ............... 424/422, 424/423, 443; 427/2.25; 604/508, 509; 623/1.11, 1.15, 11.11
See application file for complete search history.

(56) References Cited

U.S. PATENT DOCUMENTS

| | | | |
|---|---|---|---|
| 4,889,722 A | 12/1989 | Sheffield et al. | 424/450 |
| 5,116,861 A | 5/1992 | Goto et al. | 514/427 |
| 5,279,565 A | 1/1994 | Klein et al. | 604/105 |
| 5,510,077 A * | 4/1996 | Dinh et al. | 264/485 |
| 5,770,645 A | 6/1998 | Stamler et al. | 524/419 |
| 5,989,215 A * | 11/1999 | Delmotte et al. | 604/82 |
| 5,994,444 A | 11/1999 | Trescony et al. | 524/429 |
| 6,352,710 B1 * | 3/2002 | Sawhney et al. | 424/426 |
| 2002/0022046 A1 | 2/2002 | Tedeschi et al. | 424/423 |

FOREIGN PATENT DOCUMENTS

| | | |
|---|---|---|
| EP | 0 567 391 A1 | 10/1993 |
| WO | WO 95/22316 | 8/1995 |
| WO | WO 96/33757 | 10/1996 |
| WO | WO 99/38546 | 8/1999 |
| WO | WO 00/02501 | 1/2000 |
| WO | WO 00/62614 | 10/2000 |
| WO | WO 01/70199 A1 | 9/2001 |
| WO | WO 02/43786 A2 | 6/2002 |
| WO | WO 02/056904 A1 | 7/2002 |

OTHER PUBLICATIONS

J.Y. Jeremy et al., "Nitric Oxide and the Proliferation of Vasular Smooth Muscle Cells," Cardiovasc Res Aug. 15, 1999; 43(3):580-94.
Pulfer, Sharon K. et al., "Incorporation of nitric oxide-releasing crosslinked polyethyleneimine microspheres into vascular grafts," Journal of Boimedical Materials Research, vol. 37, No. 2, Nov. 1997, pp. 182-189.
Bohl, Kristyn S. et al., "Nitric oxide-generating polymers reduce platelet adhesion and smooth muscle cell proliferation," Biomaterials, vol. 21, No. 22, Nov. 15, 2000, pp. 2273-2278.
Bult, Hidde, "Restenosis: a challenge for pharmacology," Trends In Pharmacological Sciences, vol. 21, No. 7, Jul. 2000, pp. 274-279.
Grant, Maria B. et al., "Expression of IGF-1, IGF-1 receptor and TGF-B following balloon angioplasty in atherosclerotic and normal rabbit iliac arteries: An immunocytochemical study," Regulatory Peptides, vol. 79, No. 1, Jan. 1999, pp. 47-53.
Janero, David R. et al., "Nitric Oxide And Postangioplasty Restenosis: Pathological Correlates and Therapeutic Potenial," Free Radical Biology & Medicine, vol. 29, No. 12, Dec. 15, 2000, pp. 1199-1221.
Ganaha, Fumikiyo et al., "Efficient inhibition of in-stent restenosis by controlled hybrid stent-based local release of nitric oxide," Circulation, vol. 104, No. 17 Supplement, Oct. 23, 2001, p. II.506.

* cited by examiner

Primary Examiner—Lakshmi Channavajjala
(74) Attorney, Agent, or Firm—Mayer & Williams PC; David B. Bonham, Esq.; Keum J. Park, Esq.

(57) ABSTRACT

A therapeutic medical article is provided which comprises a medical article, a precursor compound and an activator compound. The medical article is adapted, upon administration to a patient, to release the precursor compound and the activator compound such that the activator compound interacts with the precursor compound and converts the precursor compound into activated form for local delivery. Specific examples of precursor and activator compound pairs include: (a) a nitrosothiol precursor and a nitric oxide donor, (b) plasminogen and plasminogen activator, and (c) fibrinogen and thrombin.

22 Claims, No Drawings

COMPOSITIONS AND TECHNIQUES FOR LOCALIZED THERAPY

FIELD OF THE INVENTION

This invention relates to compositions and techniques for localized therapy.

BACKGROUND OF THE INVENTION

At present, numerous therapeutic techniques involve the systemic delivery of one or more therapeutic agents. Systemic delivery techniques, however, are not well suited to all therapies. For instance, systemic delivery requires exposing sites other than the site of interest to a therapeutic agent. Indeed, large quantities of therapeutic agent within the entire system are often required to obtain the desired effect at a desired site. As a result, the therapeutic agent concentration at the site of interest is often limited by the detrimental effects of the agent at sites remote from the site of interest.

Systemic delivery techniques are also commonly undesirable in that the therapeutic agent is degraded and eliminated by an organ system(s) remote from the site of interest.

The above problems can be avoided by techniques in which a therapeutic agent is locally delivered to a site of interest. In response to this recognition, techniques and articles for the localized delivery of therapeutic agents to bodily tissue have been developed.

SUMMARY OF THE INVENTION

The present invention provides novel compositions and techniques for localized delivery of various therapeutic agents to the body.

According to an embodiment of the present invention, a therapeutic medical article is provided, which comprises a medical article, a precursor compound and an activator compound. The medical article is adapted, upon administration to a patient, to release the precursor compound and the activator compound such that the activator compound interacts with the precursor compound and converts the precursor compound into activated form for local delivery.

Three examples of precursor/activator compound pairs that can be used in connection with the present invention are: (a) a nitrosothiol precursor and a nitric oxide donor, (b) plasminogen and plasminogen activator, (c) fibrinogen and thrombin.

Preferred medical articles include vascular medical devices (e.g., injection catheters, infusion balloon catheters, coated balloon catheters, coated stents and coated stent-grafts) and non-vascular medical devices (e.g., polymer adhesives, tissue sealants, wound dressings, artificial tissues, extravascular wraps and implantable pumps).

In some preferred embodiments of the invention, the precursor compound and the activator compound are provided within one or more polymeric matrices that constitute all or a portion of the medical article. For example, the precursor compound and the activator compound can be provided within a single polymeric matrix, or they can be provided within different polymeric matrices.

In other preferred embodiments, the precursor compound and the activator compound can be provided within one or more populations of microparticles that are associated with the medical article. The precursor compound and the activator compound can be provided, for example, within the same population of microparticles or within distinct populations of microparticles. Moreover, the microparticles can be, for instance, provided in a suspension that is dispensed by the medical article (e.g., an injection catheter, an infusion balloon catheter, a coated balloon catheter or a coated stent).

According to another embodiment of the present invention, a therapeutic medical article like that described above is placed at an administration site on or within a patient, resulting in the release of the precursor compound and activator compound from the therapeutic medical article such that a therapeutically effective amount of the activated form of the precursor molecule is produced at the administration site.

One advantage of this aspect of the present invention is that therapeutic agents can be generated in the body at the site of interest, rather than elsewhere in the body where the therapeutic agents have little therapeutic effect or even a harmful effect.

Another advantage is that potentially harmful, highly reactive molecules can be converted at the site of interest into molecules with therapeutic characteristics.

These and other embodiments and advantages of the present invention will become immediately apparent to those of ordinary skill in the art upon reading the disclosure to follow.

DETAILED DESCRIPTION OF THE INVENTION

According to an embodiment the present invention, a precursor molecule and an activator molecule are concurrently delivered to a treatment site. As the molecules interact with one another at the treatment site, the activator molecule converts the precursor molecule into a new form, providing a therapeutic effect. Hence, as used herein, an activator molecule (also referred to herein as an activator compound) is one that converts another molecule, referred to herein as a precursor molecule (also referred to herein as a precursor compound), into a new form, referred to herein as the activated form, which is a therapeutic molecule (also referred to herein as a therapeutic agent, etc.) that provides a therapeutic effect.

Several examples of such molecules follow:

The case where the precursor molecule is a nitrosothiol precursor and the activator molecule is a nitric oxide donor that converts the nitrosothiol precursor into a nitrosothiol.

The case where the precursor molecule is a growth factor precursor and the activator molecule is an activator that converts the growth factor precursor to an active growth factor (such as TGF-beta1 or IGF-1).

The case where the precursor molecule is plasminogen and the activator molecule is a plasminogen activator.

The case where the precursor molecule is fibrinogen and the activator molecule is thrombin.

The case where the precursor molecule is a therapeutic molecule that is attached to a support and the activator molecule activates the precursor molecule by catalyzing the release of the same.

The case where the precursor molecule is activated into a therapeutic molecule by a change in temperature, a change in pressure, or by application of energy such as radiation energy, ultrasonic energy, or visible or ultraviolet light provided by a laser.

The case where the precursor molecule is an enzyme precursor (zymogen) and the activator molecule is a catalyst that activates the enzyme precursor (for instance, by causing the enzyme precursor to undergo partial proteolysis).

Medical articles are defined herein as any medical supply which can be applied to the body or inserted into the body, and which can act as a delivery vehicle for one or more agents of interest. Medical articles appropriate for the local delivery of the precursor and activator molecules onto or within the body include both vascular and non-vascular medical articles.

Preferred non-vascular medical articles include fibrin glue, other polymer adhesives and tissue sealants, wound dressings, artificial tissues, extravascular wraps, implantable pumps, bandages and wraps.

Preferred vascular medical articles include vascular catheters (for example, coated balloon catheters, injection catheters and infusion catheters), coated or uncoated stents (including vascular stents and cerebral stents), stent grafts, vascular grafts, shunts, aneurysm fillers (including Guglielmi detachable coils), intraluminal paving systems, guide wires, heart valves, balloons, embolic agents (for example polymeric particles, spheres, and liquid embolics) and filters (for example, vena cava filters).

Preferred sites for placement of the medical articles include the skin (for example, on skin wounds or over openings), coronary vasculature, peripheral vasculature, esophagus, trachea, colon, gastrointestinal tract, biliary tract, urinary tract, prostate, brain and surgical sites.

The activator and precursor molecules can be disposed upon or within the medical article in a variety of configurations including the following: (a) covalent or non-covalent attachment of one or both molecules to surface regions of the medical article, (b) disposition of one or both molecules within polymer matrices associated with the medical article, and (c) disposition of one or both molecules within fluids associated with the medical article, including solutions of one or both molecules, solid suspensions of one or both molecules, microparticle compositions (including microsphere, emulsion and liposome suspensions) comprising one or both molecules (wherein the microparticle compositions act as reservoirs for one or both molecules), and fluid gels containing one or more molecules.

Numerous techniques are known in the art by which a molecule of interest can be associated with a medical article using these and other configurations. More detailed discussions concerning certain of these configurations are found below.

Various combinations of these configurations are possible. For example, (1) the precursor and donor compound can be provided within a single matrix, within a single fluid, or on a single surface, (2) the precursor and donor compounds can be provided within distinct matrices or within distinct fluids or on distinct surfaces, (3) the activator compound can be provided in a matrix and the precursor compound can be provided in a fluid, or vice versa, (3) the activator compound can be provided in a matrix and the precursor compound can be covalently or non-covalently attached to a surface or vice versa, (5) the activator compound can be provided in a fluid and the precursor compound can be covalently or non-covalently attached to a surface or vice versa, and so forth.

Matrices are preferred reservoirs for precursor and activator compounds in many embodiments of the invention. For example, the precursor and activator molecules can be disposed within a single matrix or they can be disposed within separate matrices. The matrix or matrices can constitute, for example, an entire medical article or a distinct portion of a medical article (for example, a discrete article component, a portion of an article component, a coating on the article surface, and so forth).

The matrix configurations used in accordance with the present invention are generally selected to control release of one or both of the precursor/activator molecules by one or more of several mechanisms, including diffusion of these molecules through the matrix and release of the compound from the matrix due to matrix degradation.

Release from a matrix can be controlled in a number of ways, including the selection of the particular matrix material. Numerous matrix materials appropriate for the practice of the present invention exist in the art. Preferred matrices for the precursor and activator molecules are polymer materials, such as polycarboxylic acids, including polyacrylic acid (available as HYDROPLUS®, Boston Scientific Corporation, Natick, Mass., and described in U.S. Pat. No. 5,091,205, the disclosure of which is hereby incorporated herein by reference.); cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; polyvinyl ethers; polyvinyl aromatics; polyvinyl acetates; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene as well as other polyolefins such as polyisobutylene, polystyrenes; halogenated polyalkylenes including polytetrafluoroethylene; polyurethanes; polyorthoesters; polypeptides, including proteins; silicones; siloxane polymers; polylactic acid; polyglycolic acid; polycaprolactone; polyhydroxybutyrate valerate; coatings from polymer dispersions such as polyurethane dispersions (BAYHDROL®, etc.); fibrin; collagen and derivatives thereof; polysaccharides such as celluloses, starches, dextrans, alginates and derivatives; and hyaluronic acid. Copolymers of the above, such as ethylenevinyl acetate copolymers, copolymers of polylactic acid and polyglycolic acid, copolymers of polylactic acid and polycaprolactone, and polyethylene glycol/polyethylene oxide copolymers are also contemplated, as are derivatives and blends of the above.

The following polymers are particularly preferred: polyester polymers, copolymers and derivatives, polyolefin polymers, copolymers and derivatives, polyurethane polymers, copolymers and derivatives, polystyrene polymers, copolymers and derivatives, polyethylene glycol/polyethylene oxide copolymers and derivatives, polyvinyl alcohol polymers, copolymers and derivatives, protein-based coatings and derivatives, and hydrogel polymers, copolymers and derivatives, including natural hydrogels, such as fibrin, collagen, hyaluronic acid, proteoglycan, elastin, laminin, alginate and agarose, as well as synthetic hydrogels, such as polyHEMA and acrylate hydrogels. Polymer blends containing the above are also contemplated.

Release from a matrix can also be controlled by varying the porosity of the matrix. For instance, an additional component can be added to a matrix system to increase its porosity.

Another way of controlling release is to utilize additional matrices or matrices of different thicknesses to modulate transport. For example, transport from a first matrix material containing an activator or precursor molecule can be reduced by providing a second matrix material in the form of a barrier layer over the first matrix material. The barrier layer may or may not contain an activator or precursor molecule. Barrier layers may also be used in cases where it is desirable to effectively block diffusion from a less desirable surface of a matrix, directing diffusion to another more desirable surfaces. For example, a barrier layer can be provided on the inside surface of a matrix in the form of a stent, directing diffusion to the outer surface.

In a specific example, the precursor molecule can be placed in a first matrix in the form of a first coating and the activator molecule can be placed in a second matrix in the form of a second coating. The first and second coatings can be positioned, for instance, on distinct portions of the medical article, adjacent one another on the medical article, or layered over one another on the medical article. Optionally, additional layers can be disposed between and/or over the first and second coatings. As previously noted, these additional coatings can be used to influence the rate at which the precursor and/or activator molecule diffuses out of the coated medical article.

Microparticles are also preferred reservoirs for precursor and activator compounds in many embodiments of the invention. The activator and precursor compounds can be provided within the same population of microparticles, or they can each be provided within distinct populations of microparticles. Preferred microparticles include polymer microspheres (i.e., spheres having a diameter ranging from 1 nm to 1500 microns) and liposomes.

As with the matrices above, if desired, polymer microspheres can be provided with additional layers that act as a barrier to diffusion. Preferred materials for microspheres include polymer materials such as those discussed above, with the following polymers being particularly preferred: polyester polymers, copolymers and derivatives, polyolefin polymers, copolymers and derivatives, polyurethane polymers, copolymers and derivatives, polystyrene polymers, copolymers and derivatives, polyethylene glycol/polyethylene oxide copolymers and derivatives, polyvinyl alcohol polymers, copolymers and derivatives, protein-based coatings and derivatives, and hydrogel polymers, copolymers and derivatives, including natural hydrogels, such as fibrin, collagen, hyaluronic acid, proteoglycan, elastin, laminin, alginate and agarose, as well as synthetic hydrogels, such as polyHEMA and acrylate hydrogels. Polymer blends containing the above are also contemplated.

Preferred materials for liposomes include lipids, block co-polymers, and other biologically compatible surfactants and copolymers thereof.

Typically, the microparticles are found in a suspension dispensed by the medical article which can include adjuvants known in the art, such as phosphate buffered saline, physiological saline, and carbonate buffered saline and soluble carrier molecules such as proteins (for example, albumin), dextran, cyclodextrin, polyethylene glycol, or heparin.

The precursor and activator molecules can be established within matrices and microparticles (including microspheres and liposomes) using methods that are well known in the art.

For example, a polymer liquid is first provided that contains the precursor and/or activator molecules in dissolved, emulsified or suspended form. Then, a matrix coating can be formed on a medical article, for example, by spraying the polymer liquid onto the medical article. Alternatively, microspheres can be formed from the polymer liquid, for example, by forming an emulsion of the polymer liquid in aqueous medium, or by spraying droplets of the polymer liquid into a medium which causes the polymer liquid droplets to solidify (for example, by freezing of the solvent, physical association of the solute or chemical reaction).

Numerous techniques are also known in the art for the formation of therapeutic-agent-loaded emulsions and liposomes. For example, liposomes (lipid vesicles) are formed when thin lipid films or lipid cakes are hydrated and stacks of liquid crystalline bilayers become fluid and swell. The hydrated lipid sheets detach during agitation and self-close to form large, multilamellar vesicles (LMV) which prevents interaction of water with the hydrocarbon core of the bilayer at the edges. Once these particles have formed, reducing the size of the particle requires energy input in the form of sonic energy (sonication) or mechanical energy (extrusion). Disruption of an LMV suspensions using sonic energy (sonication) typically produces small, unilamellar vesicles (SUV) with diameters in the range of 15–50 nm. Lipid extrusion is a technique in which the lipid suspension is forced through a filter with a defined pore size to yield particles having a diameter near the pore size of the filter used. Such methods for preparing and handling liposomes are well known and are found, for example, in the Avanti Polar Lipids, Inc. Catalog, Edition IV, the disclosure of which is hereby incorporated by reference (see also http://avantilipids.com).

Specific embodiments in which the precursor molecule is a nitrosothiol precursor and the activator molecule is a nitric oxide donor will now be discussed in further detail. Nitric oxide is a highly reactive free radical, properly represented by NO♦, however, it is also commonly referred to simply as "nitric oxide" and "NO".

One advantage of these embodiments is as follows: The release of NO from a nitric oxide donor compound may not alone lead directly to a therapeutic effect. Indeed, NO can react with oxygen species generated in the body by oxidative stress (including superoxide, hydroxyl, peroxyl, alkoxyl, hydroperoxyl, and hydrogen peroxide species), resulting in products that can promote atherosclerosis or restenosis at sufficiently high concentrations. (Restenosis usually occurs within the first six months following angioplasty and is due to proliferation and migration of the cellular components of the vessel wall.) However, by making available a nitrosothiol precursor (for example, a phenolic, thiol or amine molecule), NO from the nitric oxide donor can react with such species to yield nitrosothiols, which can in turn lead to therapeutic outcomes, including restenosis prevention (e.g., by impeding proliferation of vascular smooth muscle in damaged vessels) and perfusion improvement in poorly oxygenated tissues (e.g., by relaxation of vascular smooth muscle), among many others.

Preferred nitrosothiol precursors for this embodiment of the invention are thiol molecules (i.e., molecules that inherently have one or more —SH groups or are chemically modified to contain one or more —SH groups). The thiol molecules can be small molecules, oligomers (defined in this application as molecules containing two to ten monomer units), and polymers. Preferred small molecule thiols include amino acids and pentaerythratol derivatives. Preferred oligomer thiols include perthiolated alpha-, beta- or gamma-cyclodextrin or small polypeptides. Preferred polymer thiols include proteins, polysaccharides and synthetic polymers such as polyesters and polyethylene glycol derivatives.

Methodology for forming a thiolated species from a species having one or more pendant nucleophilic groups, such as alcohols or amines, is known. See, e.g., U.S. Pat. No. 5,770,645, the entire disclosure of which is hereby incorporated by reference. Methods for producing thiol groups from alcohol groups are also disclosed in U.S. Pat. No. 4,466,914, the disclosure of which is incorporated herein by reference.

Preferred NO donors include essentially any organic or organic species that directly or indirectly produces NO, so long as NO release can be delayed until the NO donor is placed on or in the body. Some particularly preferred NO donors are as follows:

NO precursor molecules. For example, L-arginine, which does not release NO directly, but rather is an enzyme substrate that leads to the formation of nitric oxide in vivo.

Organic nitrate NO donors (i.e., organic compounds having C—O—NO$_2$ groups). Examples include nitroglycerine.

Organic nitrite NO donors (i.e., organic compounds having C—O—NO groups). Examples include amyl nitrite.

Inorganic nitroso NO donors (i.e., inorganic compounds having —NO groups). Examples include sodium nitroprusside.

Nonoate NO donors (i.e., compounds having at least one

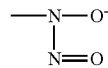

group).

Examples include substituted piperazines

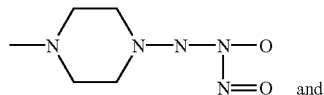

and diazeniumdiolates.

Lipophilic NO donors such as sydnonimines.

O-nitrosylated NO donors (i.e., compounds, preferably organic, having —O—NO groups). These are also known as O-nitroso compounds or in some cases organic nitrites.

S-nitrosylated NO donors (i.e., compounds, preferably organic, having an —S—NO group). These are also known as S-nitroso compounds or S-nitrosothiol compounds. Examples include: S-nitrosylated polymers, S-nitrosylated proteins, S-nitrosylated peptides (including oligopeptides and polypeptides), S-nitrosylated lipids, S-nitrosylated oligosaccharides and polysaccharides and S-nitrosylated small organic molecules (e.g., glutathione, S-nitrosylated pentaerythritol, S-nitrosylated derivatives of captopril, S-nitrosylated amino acids and S-nitrosylated alpha-, beta-, or gamma-cyclodextrin thiols).

In some embodiments, it is desirable to release catalysts (for example, transition element ions, such as copper and iron ions) that will enhance the reaction of the nitrosothiol precursor and the NO released from the NO donor. It is also desirable in several embodiments to release factors that inhibit the production of harmful oxygen containing compounds, such as those discussed above, by NO.

By disposing the activator and precursor molecules upon or within a medical article in an appropriate configuration, the nitrosothiol precursor molecules are released concurrently with the NO donor compounds. As a result, the NO produced/released from NO donor compounds reacts with the nitrosothiol precursor molecules in vivo at the treatment site, forming nitrosothiol molecules. Hence, these molecules have a therapeutic effect on a targeted disease state via a local delivery mechanism.

In some preferred embodiments, the nitrosothiol precursor (e.g., thiol) and NO donor are delivered as a fluid to a treatment site, for example, by local delivery through a medical article such as an infusion balloon catheter, a needle injection catheter or via direct injection. As noted above, one preferred fluid is a suspension of microparticles (including polymer microspheres and liposomes). In some of these embodiments, the NO donor and the thiol are co-localized within the same microparticles. In others, the NO donor is contained in one population of microparticles and the thiol is contained in another population.

In other preferred embodiments, the thiol and the NO donor are delivered from a matrix (for example, a polymer coating) associated with a medical article (such as a balloon or drug delivery catheter, or stent).

Of course other configurations and other medical articles, including stent grafts, embolic agents, bandages or wound dressings, tissue issue sealants or replacements, implantable pumps, intraluminal paving devices, extravascular sleeves, and so forth can be utilized.

As a specific example, a polymer solution consisting preferably of a copolymer of isobutylene and styrene, a thiol (such as 1% by weight of suspended glutathione particles) and a co-dissolved NO donor (such as NO-conjugated cyclodextran thiol) is dip coated onto a stent. The stent is dried and sterilized post-fabrication. The resulting stent is implanted into a patient having a stenosis of the coronary artery as a restenosis treatment.

Patients appropriate for the practice of the present invention include animal patients, preferably mammals, and more preferably humans.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A vascular medical device comprising fibrinogen as a precursor compound and thrombin as an activator compound, wherein said medical device is adapted, upon placement at an administration site within a patient, to release said precursor compound and said activator compound such that said activator compound interacts with said precursor compound and converts said precursor compound into activated form for local delivery, and wherein said vascular medical device is selected from a catheter, a stent and a graft.

2. The vascular medical device of claim 1, wherein said precursor compound and said activator compound are provided within one or more polymeric matrices constituting all or a portion of said vascular medical device.

3. The vascular medical device of claim 2, wherein said precursor compound and said activator compound are provided within a single polymeric matrix.

4. The vascular medical device of claim 2, wherein said precursor compound and said activator compound are provided within different polymeric matrices.

5. The vascular medical device of claim 2, wherein at least one of said one or more polymeric matrices comprise one or more polymers selected from polyesters polymers and copolymers, polyolefin polymers and copolymers, polyurethane polymers and copolymers, polystyrene polymers and copolymers, copolymers of polyethylene glycol and polyethylene oxide, polyvinyl alcohol polymers and copolymers, protein-based matrices and hydrogels.

6. The vascular medical device of claim 2, wherein said one or more polymer matrices are provided in the form of one or more coatings on said vascular medical device.

7. The vascular medical device of claim 1, wherein said precursor compound and said activator compound are provided within one or more populations of microparticles that are associated with said vascular medical device.

8. The vascular medical device of claim 7, wherein said precursor compound and said activator compound are provided within the same population of microparticles.

9. The vascular medical device of claim 7, wherein said precursor compound and said activator compound are provided within distinct populations of microparticles.

10. The vascular medical device of claim 7, wherein said microparticles are in a suspension dispensed by said vascular medical device.

11. The vascular medical device of claim 10, wherein said vascular medical device is selected from an injection catheter, an infusion balloon catheter, a coated balloon catheter and a coated stent.

12. The vascular medical device of claim 7, wherein said microparticles are selected from polymer microspheres and liposomes.

13. The vascular medical device of claim 2, wherein said vascular medical device is selected from an injection catheter, an infusion balloon catheter, a coated balloon catheter, a coated stent, and a coated stent-graft.

14. A method comprising:
providing a vascular medical device comprising fibrinogen as a precursor compound and thrombin as an activator compound, said vascular medical device selected from a catheter, a stent and a graft; and
placing said vascular medical device at an administration site within a patient, wherein said precursor compound and said activator compound are released from said vascular medical device and interact with one another at said administration site such that a therapeutically effective amount of an activated form of said precursor molecule is produced at said administration site.

15. The method of claim 14, wherein said precursor compound and said activated compound are administered from one or more polymeric matrices associated with said vascular medical device.

16. The method of claim 14, wherein said precursor compound and said activated compound are administered from one or more populations of microparticles associated with said vascular medical device.

17. The vascular medical device of claim 1, wherein said vascular medical device is a catheter.

18. The vascular medical device of claim 1, wherein said vascular medical device is a stent.

19. The vascular medical device of claim 1, wherein said vascular medical device is a graft.

20. The method of claim 14, wherein said vascular medical device is a catheter.

21. The method of claim 14, wherein said vascular medical device is a stent.

22. The method of claim 14, wherein said vascular medical device is a graft.

* * * * *

UNITED STATES PATENT AND TRADEMARK OFFICE
CERTIFICATE OF CORRECTION

PATENT NO. : 7,135,189 B2
APPLICATION NO. : 09/935442
DATED : November 14, 2006
INVENTOR(S) : David Knapp Page 1 of 1

It is certified that error appears in the above-identified patent and that said Letters Patent is hereby corrected as shown below:

Col. 5, Line 1, after "desirable", change "surfaces" to -- surface-- .

Col. 6, Line 10, before "LMV", delete -- an --.

Col. 6, Line 23, after "free", change "radial" to --radical --.

Col. 8, Line 18, after "tissue", delete --issue --

Signed and Sealed this

Third Day of April, 2007

JON W. DUDAS
*Director of the United States Patent and Trademark Office*